United States Patent
Jayaraman et al.

(10) Patent No.: US 9,440,910 B2
(45) Date of Patent: Sep. 13, 2016

(54) REFERENCE MARKERS FOR FESOTERODINE FUMARATE

(71) Applicant: ALEMBIC PHARMACEUTICALS LIMITED, Vadodara (IN)

(72) Inventors: Venkatraman Jayaraman, Vadodara (IN); Sundara Kalyana Balaji, Vadodara (IN); Samir Patel, Vadodara (IN); Thakor Indrajit, Vadodara (IN); Viral Parekh, Vadodara (IN); Mahesh Ladani, Vadodara (IN); Chetan Patil, Vadodara (IN); Ronak Patel, Vadodara (IN); Darshan Parmar, Vadodara (IN)

(73) Assignee: Alembic Pharmaceuticals Limited, Vadodara (IN)

( * ) Notice: Subject to any disclaimer, the term of this patent is extended or adjusted under 35 U.S.C. 154(b) by 52 days.

(21) Appl. No.: 14/370,577

(22) PCT Filed: Jan. 8, 2013

(86) PCT No.: PCT/IB2013/050141
§ 371 (c)(1),
(2) Date: Jul. 3, 2014

(87) PCT Pub. No.: WO2013/046194
PCT Pub. Date: Apr. 4, 2013

(65) Prior Publication Data
US 2014/0374284 A1   Dec. 25, 2014
US 2015/0175526 A2   Jun. 25, 2015

(30) Foreign Application Priority Data
May 18, 2012  (IN) .......................... 1511/MUM/2012

(51) Int. Cl.
*A61J 1/10*   (2006.01)
*A61K 31/222*  (2006.01)
*B65D 81/20*  (2006.01)
*B65D 81/26*  (2006.01)
*C07C 213/06*  (2006.01)
*C07C 213/10*  (2006.01)
*C07C 217/48*  (2006.01)
*C07C 219/22*  (2006.01)
*C07C 219/28*  (2006.01)
*G01N 33/15*  (2006.01)

(52) U.S. Cl.
CPC ............... *C07C 219/22* (2013.01); *A61J 1/10* (2013.01); *A61K 31/222* (2013.01); *B65D 81/2023* (2013.01); *B65D 81/264* (2013.01); *C07C 213/06* (2013.01); *C07C 213/10* (2013.01); *C07C 217/48* (2013.01); *C07C 219/28* (2013.01); *G01N 33/15* (2013.01)

(58) Field of Classification Search
CPC ... A61J 1/10; B65D 81/2023; B65D 81/264; C07C 213/06; C07C 213/10; C07C 217/48; C07C 219/22; C07C 219/28; A61K 31/222; G01N 33/15
See application file for complete search history.

(56) References Cited

FOREIGN PATENT DOCUMENTS

WO   WO2007141298   * 12/2007

* cited by examiner

*Primary Examiner* — Paul A Zucker
*Assistant Examiner* — Mark Luderer
(74) *Attorney, Agent, or Firm* — Schiff Hardin LLP

(57) ABSTRACT

The present invention relates to the new impurities of Fesoterodine, Fesoterodine symmetric dimer impurity and asymmetric dimer impurity, process for preparing and isolating thereof. The invention also deals with analytical standards and analytical methods used for the control of the production process and final quality of Fesoterodine.

9 Claims, No Drawings

REFERENCE MARKERS FOR FESOTERODINE FUMARATE

FIELD OF THE INVENTION

The present invention relates to novel compounds useful as reference markers for the analysis of Fesoterodine and pharmaceutical formulations thereof. The present invention deals with the new impurities of Fesoterodine, Fesoterodine symmetric dimer impurity (Formula II) and asymmetric dimer impurity (Formula III), which occur due to chemical instability of the target substance. Process for preparing and isolating thereof, includes methods of analytic control of the production process and quality of the target substance.

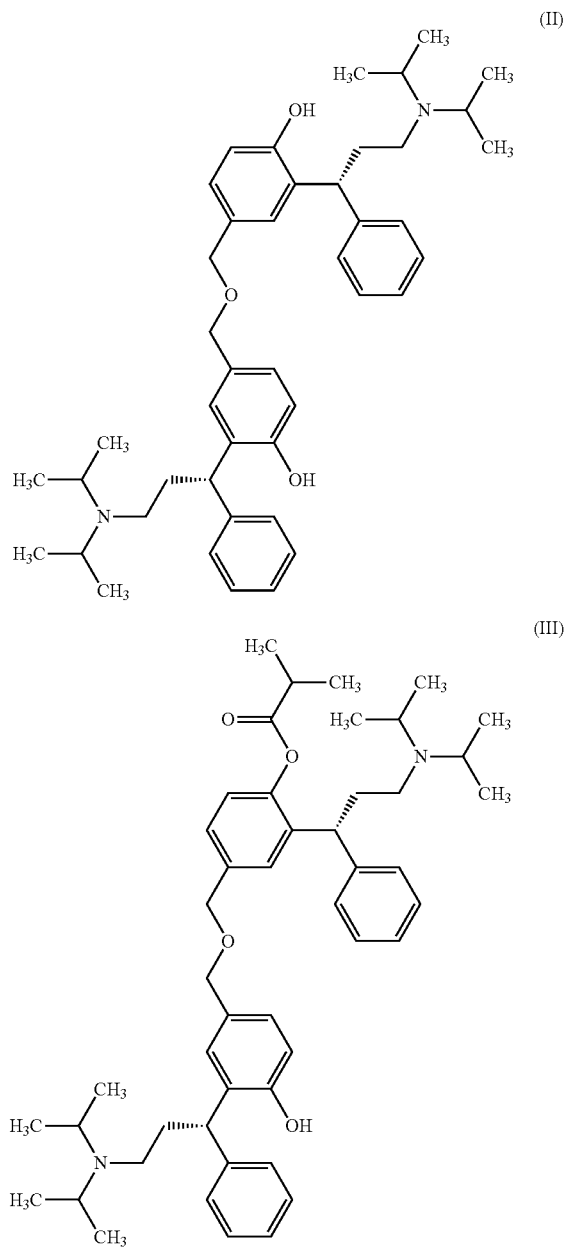

BACKGROUND OF THE INVENTION

Fesoterodine is [2-[(1R)-3-(Di(propan-2-yl)amino)-1-phenylpropyl]-4-(hydroxymethyl) phenyl]2-methylpropanoate and represented by formula (I).

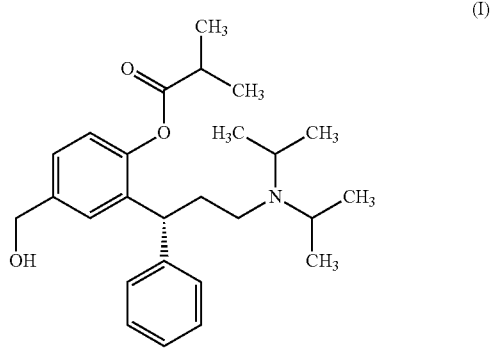 [SMILES: CC(C)C(=O)Oc1ccc(CO)cc1[C@H](CCN(C(C)C)C(C)C)c1ccccc1]

The product is marketed in the form of Fumarate salt. The current pharmaceutical product containing this drug is being sold by Pfizer using the trade name Toviaz, in the form of extended release oral tablets. Fesoterodine is cholinergic antagonist and muscarinic antagonist. Fesoterodine is rapidly de-esterified to its active metabolite, (R)-2-(3-diisopropylamino-1-phenylpropyl)-4-hydroxymethyl-phenol, or 5-hydroxy methyl tolterodine, which is a muscarinic receptor antagonist. Fesoterodine is used as Urinary Incontinence Products. It is used to treat overactive bladder.

Few processes for the synthesis of 3,3-diphenylpropylamine derivatives have been described in the literature.

Tolterodine and other 3,3-diphenylpropylamine analogs were first described in U.S. Pat. No. 5,382,660. Said patent described several methods for preparing tolterodine and its analogs generally based a process for the preparation of Tolterodine.

U.S. Pat. No. 6,713,464 disclosed a variety of 3,3-diphenylpropylamine derivatives, processes for their preparation, pharmaceutical compositions in which they are present and method of use thereof.

Fesoterodine obtained by the processes described in the above prior art does not have satisfactory purify for pharmaceutical use.

In order to secure marketing approval for a new drug, product, a drugs manufacturer must submit detailed evidence to the appropriate regulatory authority to show that the product is suitable for release on to the market. The regulatory authority must be satisfied, inter alia, that the active agent is acceptable for administration to humans and that the particular formulation which is to be marketed is free from impurities at the time of release and has an appropriate shelf-life.

Submissions made to regulatory authorities therefore typically include analytical data which demonstrate (a) that impurities are absent from the drug at the time of manufacture, or are present only at a negligible level, and (b) that the storage stability, i.e. shelf life, of the drug is acceptable. These data are usually obtained by testing the drug against an external standard, or reference marker, which is a suitably pure sample of a potential impurity or a potential degradation product.

Potential impurities in pharmaceutically active agents and formulations containing them include residual amounts of synthetic precursors to the active, agent, by-products which arise during synthesis of the active agent, residual solvent, isomers of the active agent, contaminants which were present in materials used in the synthesis of the active agent or in the preparation of the pharmaceutical formulation, or unidentified adventitious substances. Other impurities which may appear on storage include substances resulting from degradation of the active agent, for instance by oxidation, or hydrolysis.

In general, the chemical purity of the Active Pharmaceutical Ingredient (API) produced in an industrial scale is one of the critical parameters for its commercialization. The American Food and Drug Administration (FDA) as well as European authorities for drug control require API's to be free of impurities to the maximum possible extent in accordance with the instruction Q7A of ICH (International Conference on Harmonization). The purpose is to achieve maximum safety of use of the medicament in the clinical practice. National administration and control authorities usually require the content of an individual impurity in the API not to exceed the limit of 0.1%. All substances (generally referred to as impurities) contained in the API in a quantity exceeding 0.1% should be isolated and characterized in accordance with ICH recommendations. Nevertheless, the content of substances with a known structure (isolated and characterized) in a pharmaceutically acceptable ingredient should not exceed the limit of 0.15%.

The process of preparation of a pharmaceutically acceptable ingredient as well as the resulting quality of the ingredient must be under strict control in accordance with the principles of the Good Production Practice. For this control an array of methods of analytic chemistry are used among which separation, techniques allowing very sensitive analyzing of the ingredient as well as its mixtures with other substances occupy a prominent position. High Performance Liquid Chromatography (HPLC), ultra-high performance liquid chromatography (UPLC) or Gas Chromatography (GC) is usually used for this purpose.

Impurities present in the API are then determined by the relative position, of the peak in the HPLC or GC chromatogram while the peak position is usually expressed as the time (in minutes) necessary for the imparity to travel from the point of sample injection to the HPLC or GC column filled with a suitable sorbent to the detection place. The time necessary for a chemical substance (e.g. API or impurity) to get from the injection, point to the detector under standard conditions is referred to as the "retention time", Retention times (RT) related to the retention-time of a standard (usually RT of the API) are called "relative, retention times". The relative retention time (RRT) of the API usually, takes the value 1, components that need a shorter time to travel to the detector manifest lower relative retention times than 1 while components travelling more slowly exhibit higher relative retention, times than 1. Under standard conditions the relative retention times are considered, as standard characteristics of the analyzed substance, i.e. they only depend on the chemical structure of the particular constituent. The position of the peak in the chromatogram, or the retention time, is only a quality parameter that does not provide information about the quantity of the analyzed substance.

For reliable determination of the content of the analyzed constituent it is necessary to have an analytical standard of the substance. The result of the quantity determination is usually expressed in percent by weight. If standards of impurities (including raw materials, intermediate products and optic isomers) are not available, it is very difficult to determine their actual content in the API, to find an acceptable analytic method and to perform its validation. Without, the possibility of reliable quality assurance of the API it is not possible to control the process of its production, and use the obtained, substance for the preparation of a pharmaceutical formulation.

Standards of impurities, analytic methods of chemical purity of the API and quantity determination methods are extremely important for the control of the production process and consequently for successful commercialization of the product.

The solution presented by us represents a new and convenient method of determining chemically pure Fesoterodine (I), including methods of analytical control of the production process and quality of the target substance. Also provides the packaging condition that improves its stability.

SUMMARY OF THE INVENTION

The invention provides especially analytical standards and analytical methods used for the control of the production process and final quality of Fesoterodine Fumarate.

One aspect of the present invention is to provide a method of testing the purity of a sample of Fesoterodine or its salt or a pharmaceutical dosage form comprising Fesoterodine, which method comprises assaying the said sample for the presence of compound of formula II or compound of formula III.

Another aspect of the present invention is to provide a method of testing the purity of a sample of Fesoterodine or its salt or a pharmaceutical dosage form comprising Fesoterodine, which method, further comprises using a sample of compound of formula II or compound of formula III having a purity level of at least 80% as a reference marker.

Another aspect of the present invention is to provide compound of formula II or its salt or its enantiomer.

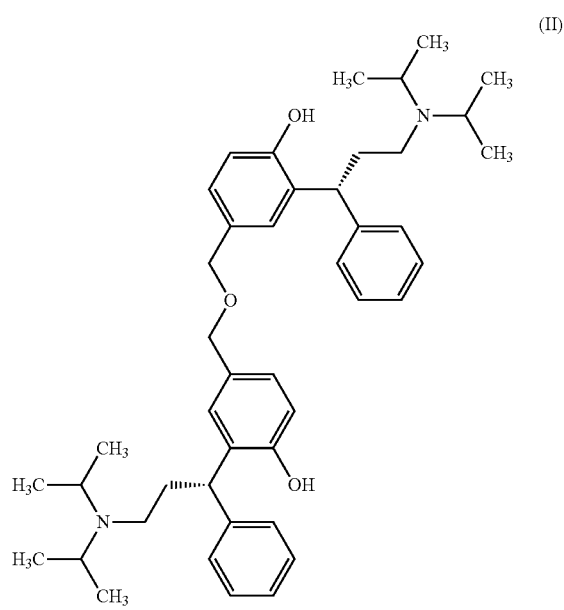 [SMILES: CC(C)N(CC[C@H](c1ccccc1)c1cc(COCc2ccc(O)c([C@@H](CCN(C(C)C)C(C)C)c3ccccc3)c2)ccc1O)C(C)C]

Another aspect of the present invention is to provide compound of formula III or its salt or its enantiomer.

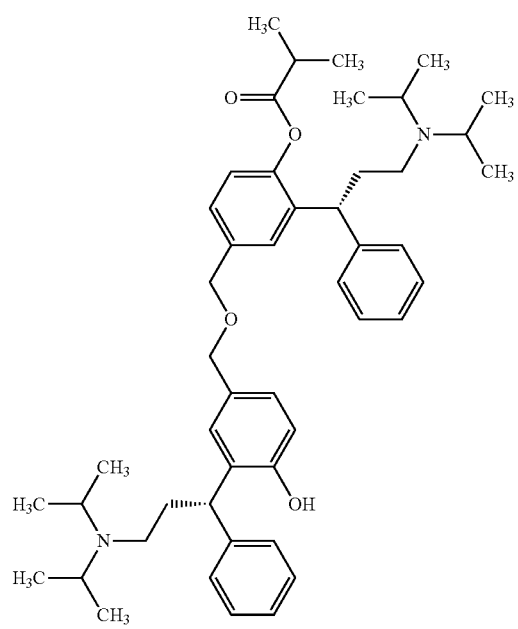

(III)

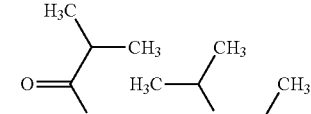

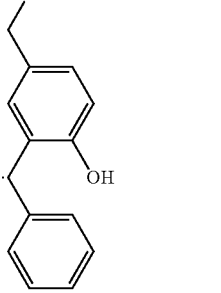

(III)

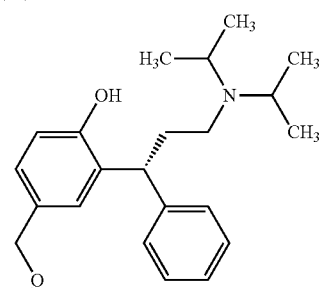

(II)

Another aspect of the present invention is to provide, sample of a compound is in substantially pure form.

Another aspect of the present invention is to provide method, of preparation of the compound of formula II and/or compound of formula III, comprising condensation of Fesoterodine base or its salt with dihydroxy compound formula VI.

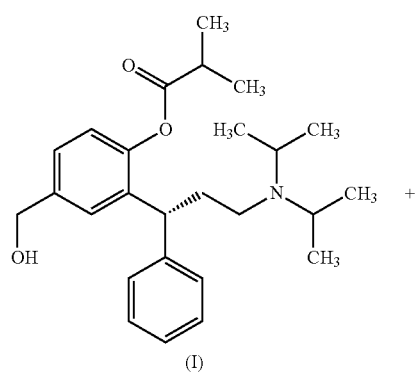

(I)

Another aspect of the present invention is to provide method of preparation of the compound of formula II, comprising self condensation of dihydroxy impurity.

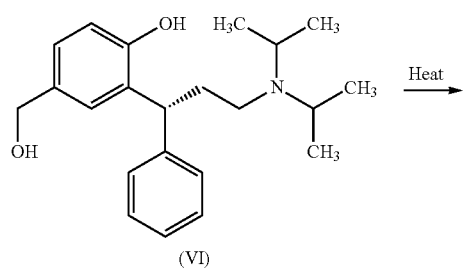

(VI)

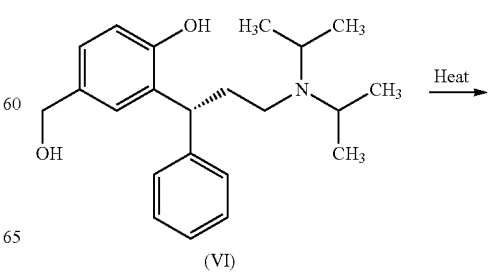

(VI)

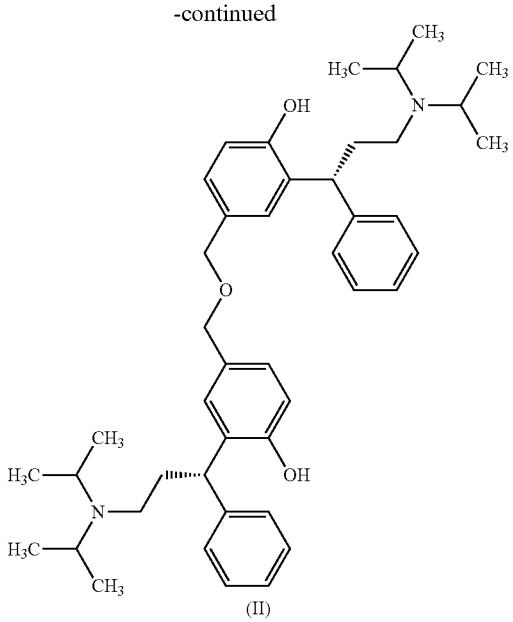

(II)

Another aspect of the present invention is to provide compound of formula V or its salt or its enantiomer.

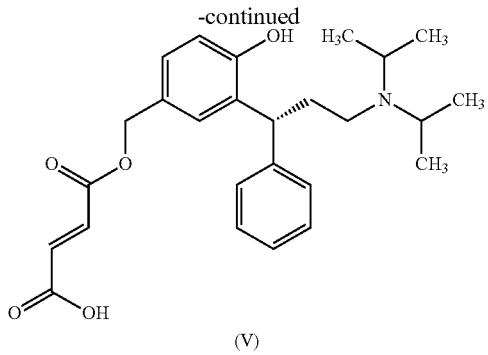

(V)

Another aspect of the present invention is to provide method of preparation of the compound of formula V, comprising condensation of dihydroxy compound of formula (VI) with fumaric acid.

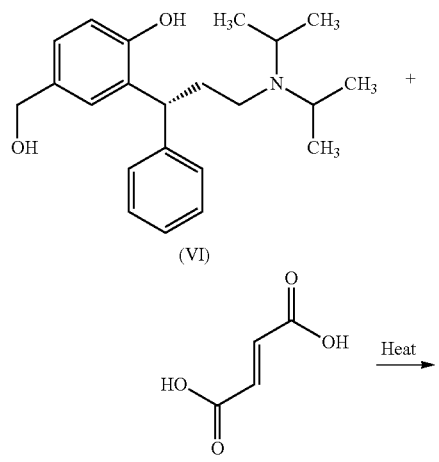

Another aspect of the present invention is to provide a pharmaceutical composition comprising fesoterodine or a pharmaceutically acceptable salt thereof, and an amount of a compound of formula (II) and/or (III) and/or (V).

Another aspect of the present invention is to provide an isolated specific impurity of Fesoterodine Fumarate, selected from the group including formula II, III and formula V and their salts, characterized by chemical purity of more than 50% for use in setting the analytic methods designed for quality control of Fesoterodine Fumarate.

Another aspect of the present invention is to provide a vacuum sealed pack comprising Fesoterodine Fumarate wherein the Fesoterodine Fumarate is packaged in oxygen and moisture impermeable package.

Another aspect of the present invention is to provide a vacuum sealed, pack wherein the pack comprises three layers.

Another aspect of the present invention is to provide a vacuum sealed pack wherein the Innermost layer comprises the (LDPE) low density polyethylene bag or (HM, HDPE) high molecular high-density poly ethylene which is vacuum sealed and sealed using heat induction.

Another aspect of the present invention is to provide a vacuum sealed pack wherein, the Middle layer is a special plastic bag of (HM, HDPE) high molecular high-density poly ethylene or Triple Laminate Sunlight Barrier (TLSB) bag comprises moisture absorber and nitrogen gas purged and sealed using heat induction.

Another aspect of the present invention is to provide a vacuum sealed pack wherein the Outermost layer is triple laminated aluminum bag inside black coated or quad laminate ultra barrier (QLUB) bag comprises moisture absorber and nitrogen gas purged and sealed using heat induction.

Another aspect of the present invention is to provide a vacuum sealed pack wherein the moisture absorber is selected from the group consisting of canister desiccant, desiccant, activated carbon, silicas, zeolites, molecular sieves, hydrogels, calcium oxide and diatomaceous earth.

Another aspect of the present invention is to provide a vacuum seated pack wherein the bag is put in rigid container.

Another aspect of the present invention is to provide a vacuum sealed pack wherein the rigid container is non-airtight/air-right plastic/metal drums, HDPE (high density polyethylene), PP (polypropylene), LDPE (low density polyethylene), PET, PVC (polyvinyl chloride) drum.

Another aspect of the present invention is to provide an improved packing condition for Fesoterodine Fumarate API comprises layers as
  a. Innermost: LDPE bag under vaccumised and heat sealed followed by another LDPE bag under vaccumised and heat sealed.

b. Middle: Special plastic bag of HMHDPE having desiccant, under nitrogen gas purged and heat sealed.
c. Outermost: Triple laminated aluminum bag inside black coated having desiccant, under nitrogen gas purged and heat sealed then packed in HDPE drum Another aspect of the present invention is to provide an unproved packing condition for Fesoterodine Fumarate API comprises layers as
a. Innermost: HMHDPE bag vaccumised and heat sealed.
b. Middle: Triple Laminate Sunlight Barrier (TLSB) bag having canister desiccant, nitrogen gas purged with vacuum and heat sealed.
e. Outermost: quad laminate ultra barrier (QLUB) bag having canister desiccant, nitrogen gas purged with vacuum and heat sealed, then packed in HDPE drum.

DETAILED DESCRIPTION OF THE INVENTION

The Fesoterodine Fumarate must be analysed for purity, typically by UPLC, HPLC or GC analysis, to determine if it is suitable for continued processing or ultimately for use in a pharmaceutical product.

There is eight main known impurities of Fesoterodine Fumarate are available which are characterizes as below.

(i) (R)-2-(3-diisopropylamino-1-phenylpropyl)-4-hydroxymethyl phenol hydrogen fumarate (Impurity-A) which has the following, structure;

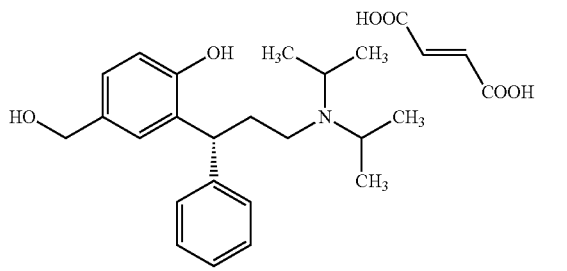

The impurity-A is detected and resolved from fesoterodine fumarate by UPLC with a relative retention time (hereafter referred as RRT) of 0.25.

(ii) (±)-Isobutyrate-2-(3-diisopropylamino-1-phenylpropyl)-4-isobutyrylloxy methylphenylester hydrogen fumarate (Impurity-B), which, has the following structure;

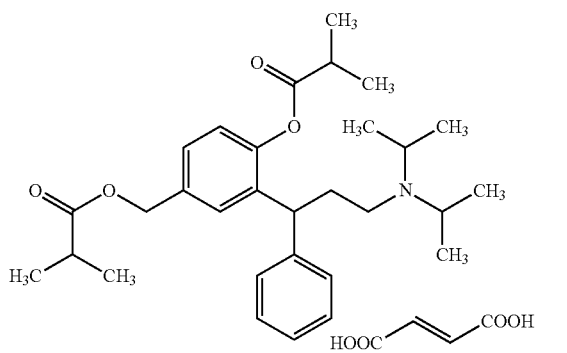

Impurity-B is detected and resolved from fesoterodine fumarate by UPLC with an RRT of 2.28.

(iii) (R)-[4-Benzyloxy-3-(3-diisopropylamino-1-phenylpropyl)-phenyl]-methanol hydrogen fumarate. (Impurity-C), which has the following structure:

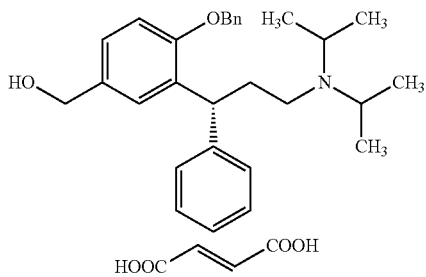

The impurity-C is detected and resolved from fesoterodine fumarate by UPLC with an RRT of 1.16.

(iv) (±)3-(3-(diisopropylamino)-1-phenylpropyl)-4-(isobutyryloxy) benzoic acid hydrogen fumarate (Impurity-E), which has the following structure:

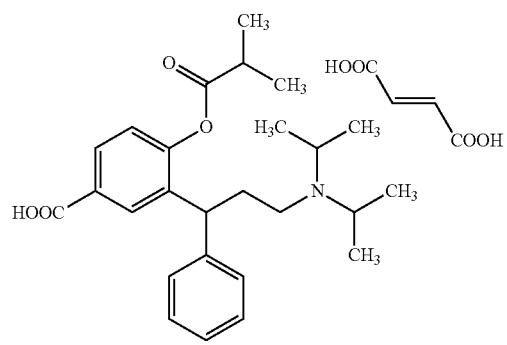

The impurity-E is detected and resolved from fesoterodine fumarate by UPLC with an RRT of 0.18.

(v) (±)-2-(3-(diisopropylamino)-1-phenylpropyl)-4-formylphenyl isobutyrate hydrogen fumarate (Impurity-F), which has the following structure:

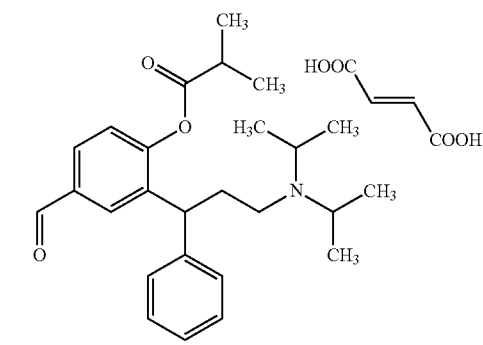

The Impurity-F is detected and resolved from fesoterodine fumarate by UPLC with an RRT of 1.46.

(vi) 4-[(3-(3-diisopropylamino-1-phenylpropyl)-4-(2-isobutyroyloxyphenyl)-methoxy]-4-oxobut-2-enoic acid hydrogen, fumarate (Impurity-G), which has the following structure:

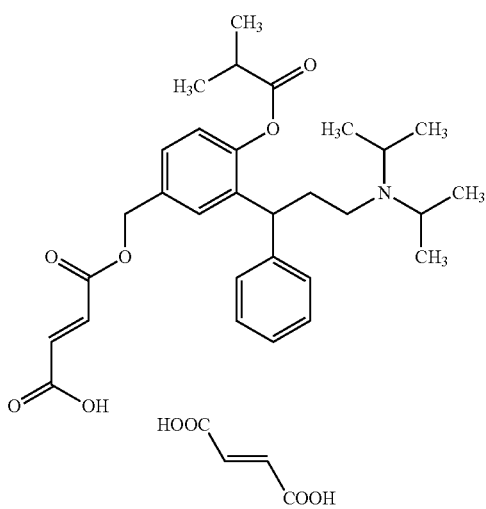

The impurity-G is detected and resolved from fesoterodine fumarate by UPLC with an RRT of 0.27.

(vii) R-(+)-N,N-diisopropyl amine-3-(2)-Benzyloxy-5-Methylphenyl)-3-Phenyl propyl amine hydrogen fumarate (Impurity-H) which has the following structure:

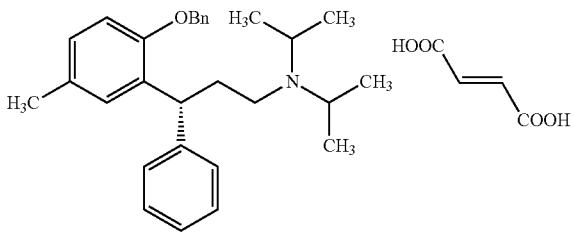 [SMILES: Cc1ccc(OCc2ccccc2)c([C@H](CCN(C(C)C)C(C)C)c2ccccc2)c1 ; O=C(O)/C=C/C(=O)O]

Impurity-H is detected and resolved from fesoterodine fumarate by UPLC with an RRT of 2.67.

(viii) (R)-2-(3-(diisopropylamino)-1-phenylpropyl)-4-methylphenyl isobutyrate hydrogen fumarate (Impurity-I) which has the following structure:

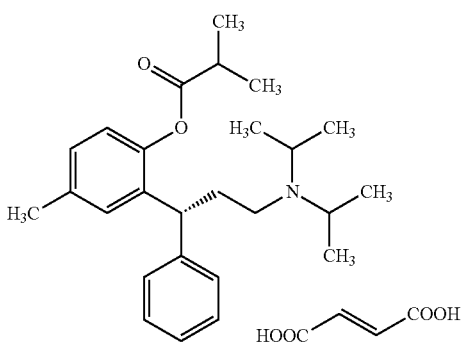

Impurity-I is detected and resolved from fesoterodine fumarate by UPLC with an RRT of 1.93.

Above all are the known impurities of Fesoterodine Fumarate API. During the stability study of Fesoterodine Fumarate present inventors have found two novel impurities of Fesoterodine Fumarate.

During analysis of the stability samples of fesoterodine fumarate, after 2-6 months stability at 25° C. and above temperature, the unknown impurity (1.82 RRT) detected which was not observed during initial analysis.

Present inventors carried out the stability study of Fesoterodine Fumarate at different conditions and summarized the table shown below which easily indicate how the impurity at 1.82 RRT is increasingly generated.

Stability Study of Fesoterodine Fumarate at 25° C.+/−2° C. 60%+/−5% RH

| Time duration | Dihydroxy impurity (active metabolite) | 0.29 RRT (Fumaric acid ester) | 1.82 RRT | Purity of Fesoterodine fumarate |
| --- | --- | --- | --- | --- |
| Initial | 0.07% | 0.03% | ND | 99.69% |
| 1 month | 0.15% | 0.05% | ND | 99.52% |
| 2 month | 0.27% | 0.07% | ND | 99.38% |
| 3 month | 0.40% | 0.08% | 0.01% | 99.25% |
| 4 month | 0.53% | 0.07% | 0.02% | 99.11% |
| 6 month | 1.02 | 0.12% | 0.11% | 98.42% |

Stability Study of Fesoterodine Fumarate at 40° C.+/−2° C. 75%+/−5% RH

| Time duration | Dihydroxy impurity (active metabolite) | 0.29 RRT 0.29 RRT (Fumaric acid ester) | 1.82 RRT | Purity of Fesoterodine fumarate |
| --- | --- | --- | --- | --- |
| Initial | 0.07% | 0.03% | ND | 99.69% |
| 1 month | 0.64% | 0.10% | 0.06% | 98.92% |

Stability Study of Fesoterodine Fumarate at 30° C.+/−2° C. 65%+/−5% RH

| Time duration | Dihydroxy impurity (active metabolite) | 0.29 RRT (Fumaric acid ester) | 1.82 RRT | Purity of Fesoterodine fumarate |
| --- | --- | --- | --- | --- |
| Initial | 0.07% | 0.03% | ND | 99.69% |
| 1 month | 0.23% | 0.06% | ND | 99.43% |
| 2 month | 0.45% | 0.09% | 0.02% | 99.15% |
| 3 month | 0.71% | 0.10% | 0.07% | 98.84% |
| 4 month | 0.76% | 0.09% | 0.11% | 98.74% |

Stability Study of Fesoterodine Fumarate at 2-8° C.

| Time duration | Dihydroxy impurity (active metabolite) | 0.29 RRT (Fumaric acid ester) | 1.82 RRT | Purity of Fesoterodine fumarate |
| --- | --- | --- | --- | --- |
| Initial | 0.07% | 0.03% | ND | 99.69% |
| 3 month | 0.11% | 0.04% | ND | 99.61% |
| 6 month | 0.15% | 0.05% | ND | 99.52% |

Stability Study of Fesoterodine Fumarate with 30% Dihydroxy Impurity

| | Dihydroxy impurity (active metabolite) | 0.29 RRT (Fumaric acid ester) | 1.82 RRT | Purity of Fesoterodine fumarate |
| --- | --- | --- | --- | --- |
| In open dish At 40° C. +/− 2° C. 75% +/− 5% RH for 192 hours | 38.58% | 0.42% | 1.89% | 57.63% |

-continued

| | Dihydroxy impurity (active metabolite) | 0.29 RRT (Fumaric acid ester) | 1.82 RRT | Purity of Fesoterodine fumarate |
|---|---|---|---|---|
| In RBF with methyl ethyl ketone and water at 800 C. for 30 hrs | 37.53% | 0.35% | 1.70% | 58.59% |

During Stability study of Fesoterodine Fumarate at 25° C.+/−2° C. 60%+/−5% RH present inventors found unknown impurity at 1.82 RRT, this impurity was isolated by preparative HPLC. Purity of the isolated solid was found to be more than 80%. Structure of impurity was confirmed by LC-MS, 1H and 13C NMR spectroscopy. On the basis of spectral data, the structure of the impurity was confirmed as asymmetric dimer impurity (compound of formula III), Compound of formula III

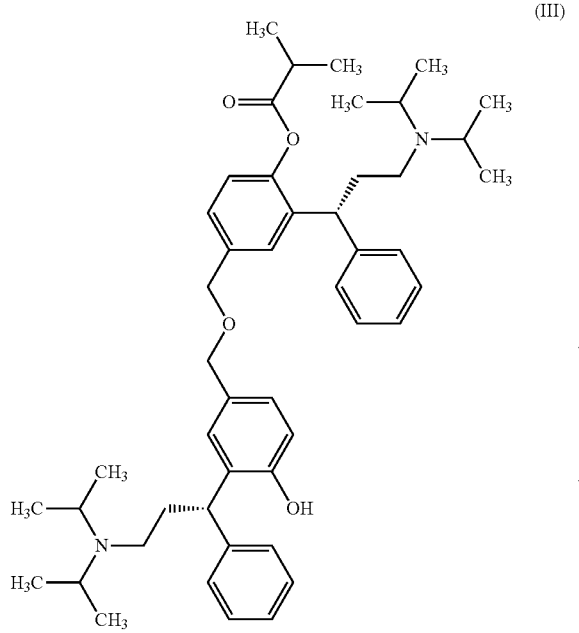

Further, during Stability study of Fesoterodine Fumarate at 40° C.+/−2° C. 75%+/−5% RH present inventors found unknown impurity at 1.82 RRT. When they tried to isolate this impurity by preparative HPLC, during this process they surprisingly found that there are two impurities which are present at same RRT. They can differentiate these two impurities using preparative HPLC. They isolated both the impurities and structures of impurities were confirmed by LC-MS, 1H and 13C NMR spectroscopy. On the basis of spectral data, the structure of the impurities was confirmed as Fesoterodine symmetric dimer impurity (compound of formula II) and asymmetric dimer impurity (compound of formula III),

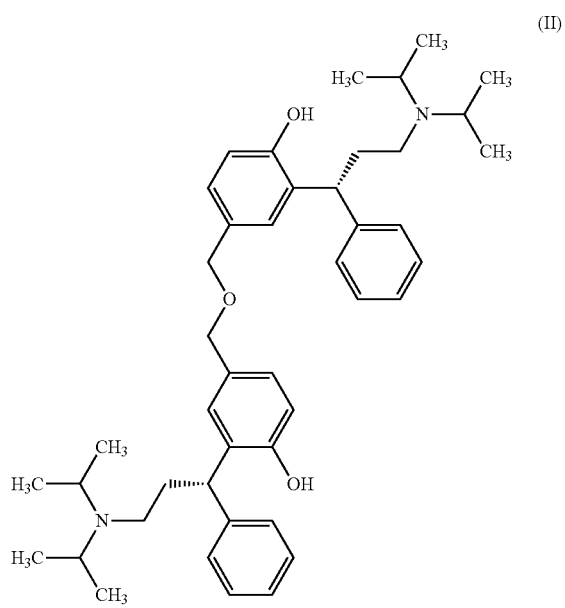 [SMILES: CC(C)N(CC[C@H](c1ccccc1)c1cc(COCc2ccc(O)c([C@@H](CCN(C(C)C)C(C)C)c3ccccc3)c2)ccc1O)C(C)C]

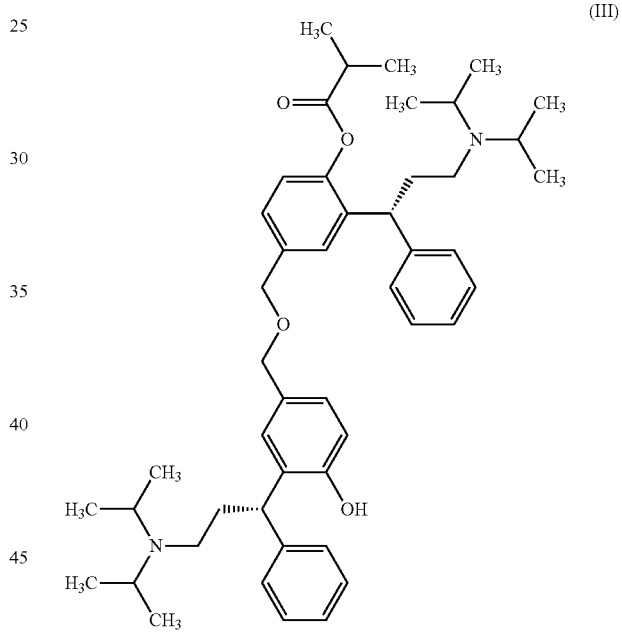

These impurities were unambiguously confirmed by synthesis also.

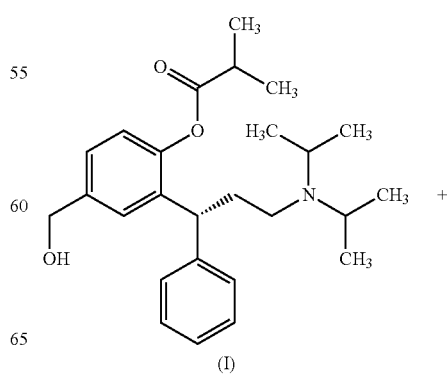

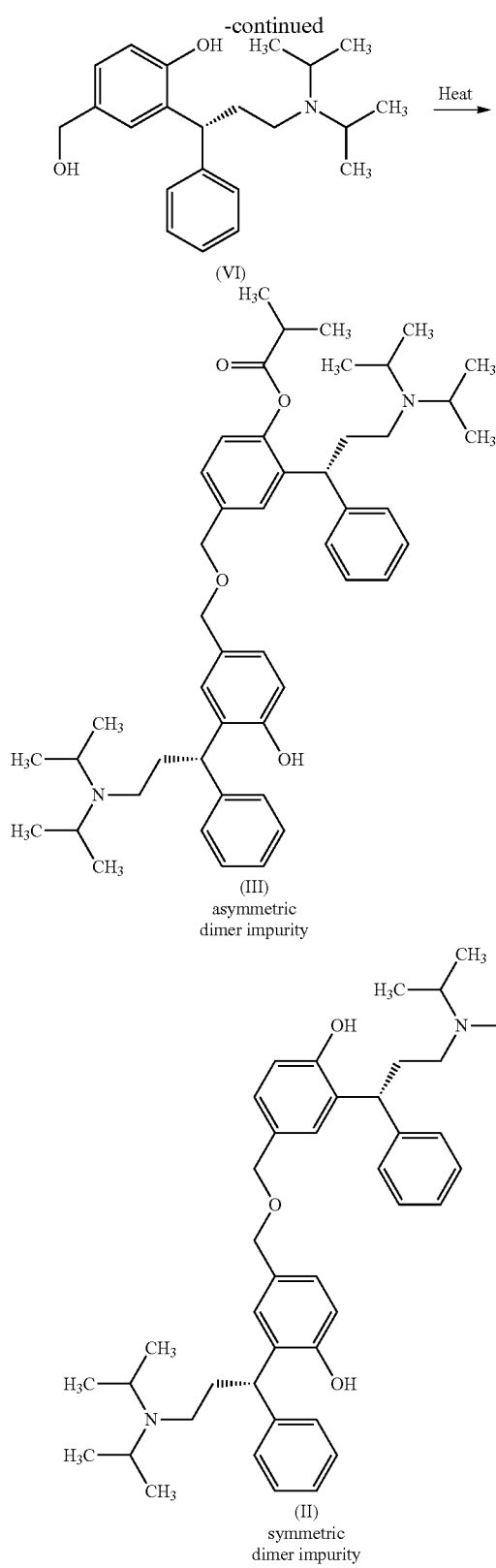

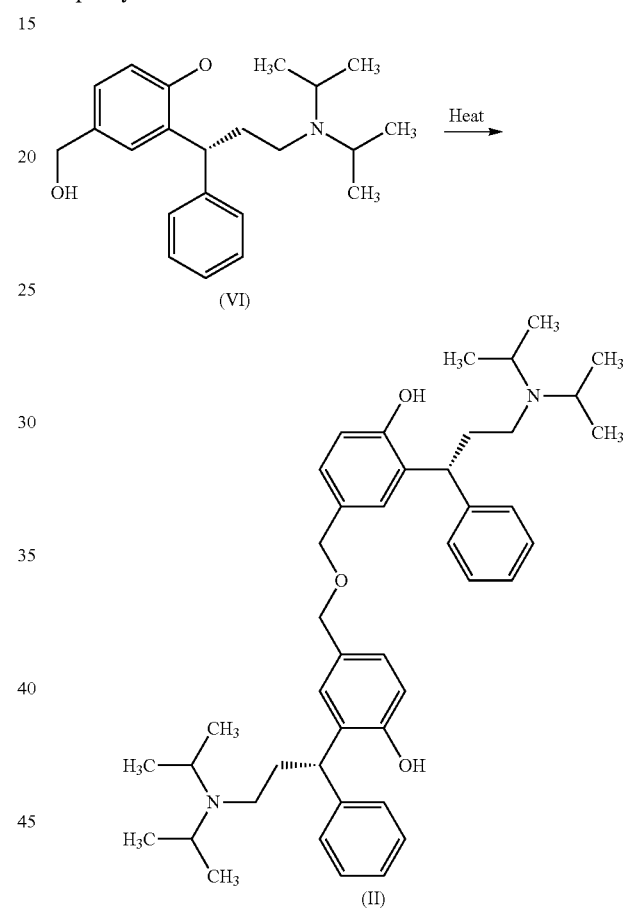

ents, this was achieved by a procedure characterized by condensation of Fesoterodine base with dihydroxy impurity in presence of heat. These impurities are then separated using column chromatography.

By means of this method a highly chemically pure analytical standard was obtained that can be used for the purposes of setting the determination methods of chemical purity as well as the content of the analyzed substance in any sample. The process used for the preparation of the analytical standard of compound of formula II and compound of formula III is described in example.

There is another method of preparation of the compound of formula II, comprising self condensation of dihydroxy impurity.

There is one more possible impurity is of the compound of formula IV, can synthesize by self condensation of fesoterodine.

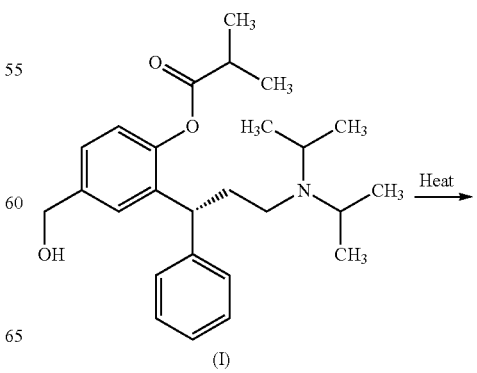

For the control of the production process, especially for reliable setting of analytic methods it was necessary to prepare an analytical standard of compound of formula II and compound of formula III with acceptable chemical purity and content. To achieve an acceptable quality of the standard the substance had to be free of all foreign constitu-

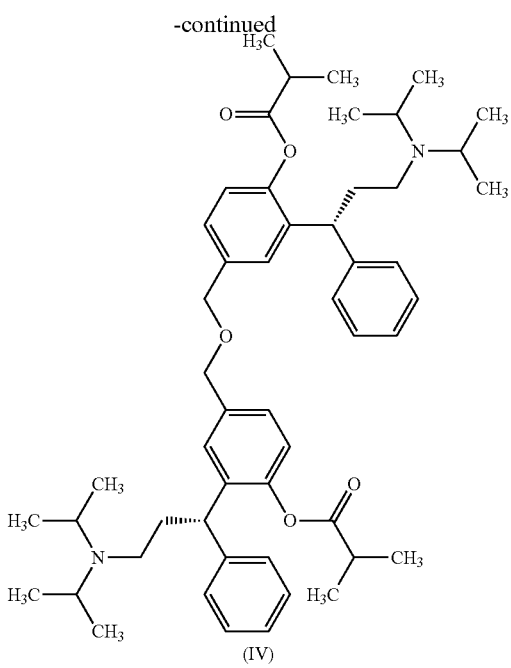

(IV)

In the case of pharmaceutically acceptable. Fesoterodine (I) the content of the Fesoterodine symmetric dimer impurity (formula II) and asymmetric dimer impurity (formula III), in the target substance must not exceed the limit of 0.15%. Due to the setting of analytic methods for determination of optical purity it is usually necessary to synthesize the standards of both the dinner impurities.

The object of the invention will be explained in a more detailed way by means, of the following Examples, which, however, do not have any influence on the scope of the invention defined in the claims.

EXAMPLES

Preparation of Compound of Formula II and Formula III

Charge Fesoterodine base (3.0 gm), dihydroxy impurity (2.0 gm) at 25-35° C. Heat the reaction mixture to dissolve solid and maintain it at 60-70° C. for 8 hrs. Cool the reaction mixture at 25° C.-35° C. Charge ethyl-acetate (25 ml) and heptane (25 ml) in reaction mass at 25-35° C. Stir the reaction mass at 25-35° C. for 2.0 hrs. Decant the upper solvent layer and then distill out the residual solvent at 30° C. under vacuum. Separated the compound of Formula II and compound of formula III using column chromatography (mobile phase-ethyl acetate:hexane:diethyl amine)

Analytical Data of Asymmetric Dimer Impurity (III)

1HNMR (CDCl3 300 MHz) δ: {dd, 1.332 CH—(CH3)2}, {dd, 1.12 CH—(CH3)2}, {dd, 1.08 CH—(CH3)2}, {dd, 0.89 CH—(CH3)2, CH—(CH3)2}, {m, 2.0 3CH—(CH3)2}, {m, 2.32 2CH—(CH3)2, CH2-CH2}, {t, 2.76 CH2-CH2}, {t, 2.95 CH2-CH2}, {t, 3.23 CH2-CH2-CH2}, {s, 4.24 CH2-O}, {s, 4.34 CH2-O}, {t, 4.09 CH-phenyl}, {t, 4.09 CH-phenyl}, {t, 4.51 CH-phenyl}, {m, 6.69-7.31 16 aromatic CH}, Mass: 735.8 (M+1)

13CMR (APT): (CDCl3) δ: 175.12 (C═O), 132.46-155.34 (8 quaternary aromatic carbon), 118.32-128.438 (12 aromatic CH-carbon), 33.04-71.89 (6 CH2), 34.12-41.70 (3 CH), 47.85-48.61 (2 CH), 18.88-20.54 (6 CH3)

Analytical Data of Symmetric Dimer Impurity (II)

1HNMR (CDCl3 300 MHz) δ: {d, 1.10 2CH—(CH3)2,}, {d, 1.15 2CH—(CH3)2,}{m, 2.09 2CH—(CH3)2}, {m, 2.73 2CH—(CH3)2}, {m, 2.37 2CH2-CH2}, {m, 3.26 2CH2}, {dd, 4.50 2CH-Phenyl}, {dd, 4.16 2CH2-O}, {m, 6.68-7.33 16 aromatic CH}, Mass: 665.7 (M+1)

13CMR (APT): (CDCl3) δ: 132.46-155.34 (4 quarternary aromatic carbon), 118.21-128.42 (6 aromatic CH-carbon), 33.02-71.58 (3 CH2), 39.30-47.86 (2 CH), 19.44-19.84 (2 CH)

Preparation of Compound of Formula V

Charged dihydroxy impurity (5.0 gm), fumaric acid 2.547 gm) at 25-35° C. and heat the mixture at 110-115° C. for 24-48 hrs. Cooled the reaction mixture at 25° C.-35° C. Purified the above compound through column chromatography or preparative HPLC and collect fraction and distilled out at 30° C. and degas it for 2 hrs at 30° C. wt of impurity around 500 mg.

Analytical Data of Fumaric Acid Ester Impurity (V)

1HNMR (DMSO 300 MHz) δ: {d, 1.00 CH—(CH3)2}, {m, 2.2 CH—(CH3)2}, {m 2.69 CH2-CH2}, {m, 3.29 CH2-CH2}, {s, 5.02 2CH2-O}, {t, 4.32 1CH-phenyl}, {d, 6.76 1CH═CH}, {d, 6.71 1CH═CH}, {m, 7.02 8 Aromatic CH}, {s, 8.25 OH}, Mass: 440.1 (M+1)

Analytical Experimental

The LC system, used for method development and forced degradation studies and method validation was Waters-Alliance (manufactured by Waters India Ltd) LC system with a photo diode detector. The out put signal was monitored and processed using Empower software system (designed by Waters India) on IBM computer (Digital Equipment Co).

The chromatographic column used was a Waters Aquity BEH C18 100 mm×2.1 mm column with 1.7 μm particles. The mobile phase consists buffer (1.4 g of Disodium hydrogen phosphate in 1000 mL of water pH-8.0 with ortho phosphoric acid), and solvent is acetonitrile. The flow rate of the mobile phase was kept at 0.3 ml/min. beginning with the gradient ratio of mobile phase buffer and solvent 50:50 (v/v), system was continued at the same ratio for 2 minutes. The ratio was changed linearly 30:70(v/v) within 7 minutes and again system was continued at the same ratio for 9 minutes. After 1.5 minutes the initial gradient of 50:50 is for 2.5 minutes to be conditioned far every analysis. The column temperature was maintained at 45° C. and the wavelength was monitored at a wavelength of 220 nm. The injection volume was 3 μL for related substances determination. Acetonitrile was used as diluent during the standard, and test samples preparation.

Packaging Conditions

To avoid degradation during stability, following is the recommended packing condition for Fesoterodine Fumarate:

Innermost: LDPE bag under vaccumised and heat sealed followed by another LDPE bag under vaccumised and heat sealed.

Middle: Special plastic bag of HMHDPE having desiccant, under nitrogen gas purged and heat sealed.

Outermost: Triple laminated aluminum, hag inside black coated having desiccant, under nitrogen gas purged and heat sealed then packed in HDPE drum Further better packing condition to avoid degradation of Fesoterodine Fumarate:

Innermost: HMHDPE bag vaccumised and heat sealed.

Middle: TLSB bag having canister desiccant, nitrogen gas purged with vacuum and heat sealed.

Outermost: QLUB bag having canister desiccant, nitrogen gas purged with vacuum and heat sealed, then packed in HDPE drum.

Material should be packed at 25° C.+/−2° C. 35%+/−5% RH

The invention claimed is:

1. An isolated specific impurity of Fesoterodine Fumarate, compound of formula (II), characterized by chemical purity of more than 50% for use in setting the analytic methods designed for quality control of Fesoterodine Fumarate

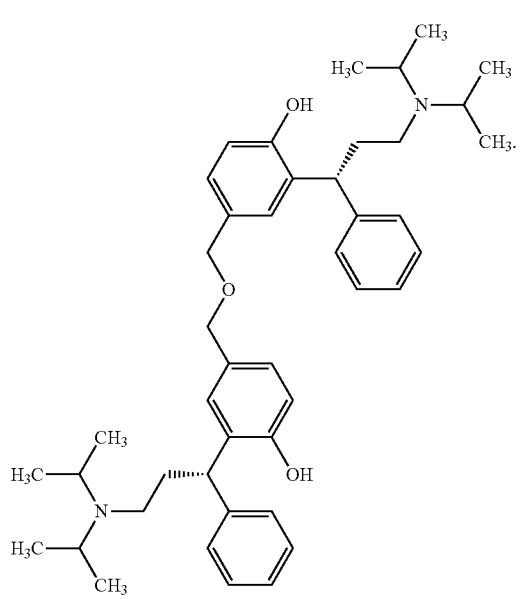

2. A process for preparation of the compound of formula comprising:
(a) self condensation of dihydroxy compound (VI); or

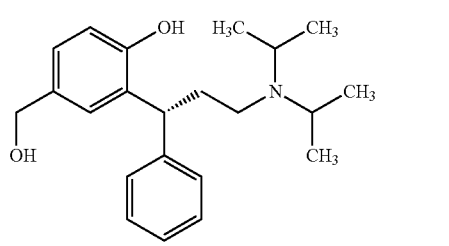

(b) condensation of Fesoterodine base (I) or its salt with dihydroxy compound (VI).

3. A vacuum sealed pack comprising Fesoterodine Fumarate which is free of compound of formula (II), wherein the Fesoterodine Fumarate is packaged in a moisture and oxygen impermeable package

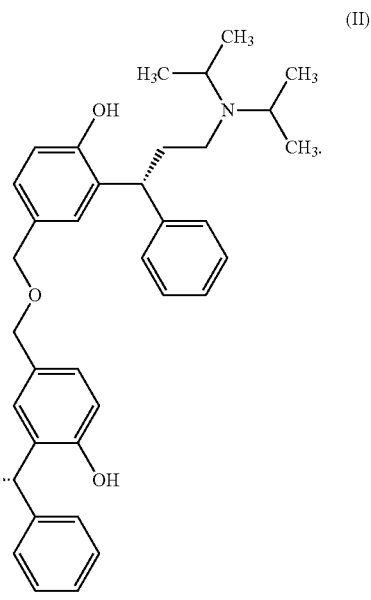

4. An isolated specific impurity of Fesoterodine Fumarate, compound of formula (III), characterized by chemical purity of more than 50% for use in setting the analytic methods designed for quality control of Fesoterodine Fumarate

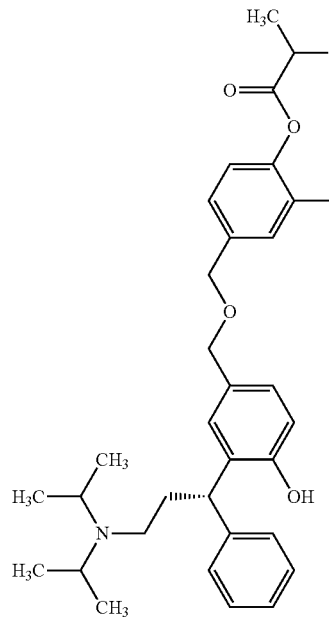

5. A process for preparation of the compound of formula (III), comprising condensation of Fesoterodine base (I) or its salt with dihydroxy compound (VI)

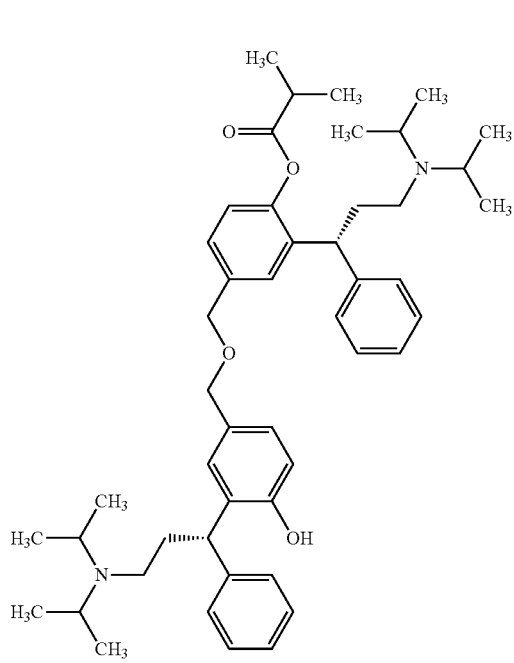

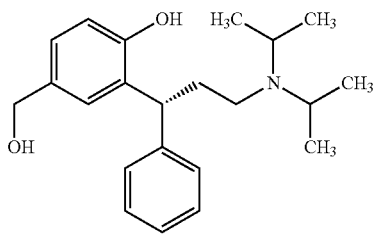

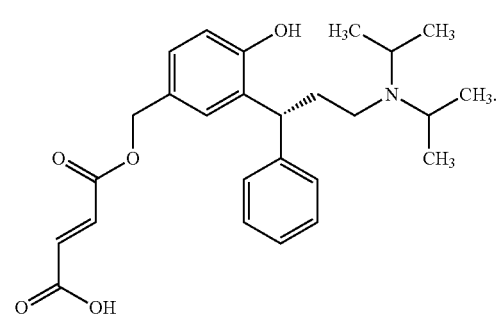

7. A compound of formula (V) or its salt or its enantiomer

8. An isolated specific impurity of Fesoterodine Fumarate, compound of formula (V) as claimed in claim 7, characterized by chemical purity of more than 50% for use in setting the analytic methods designed for quality control of Fesoterodine Fumarate.

9. A process for preparation of the compound of formula (V) as claimed in claim 7, comprising condensation of dihydroxy compound of formula (VI) with fumaric acid

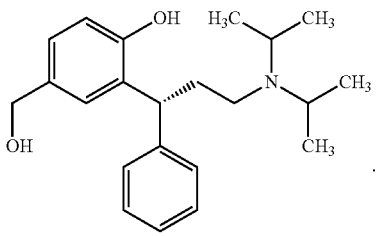

6. A vacuum sealed pack comprising Fesoterodine Fumarate which is free of compound of formula (II); wherein the Fesoterodine Fumarate is packaged in moisture and oxygen impermeable package

* * * * *